United States Patent [19]

Hu

[11] Patent Number: 5,473,655
[45] Date of Patent: Dec. 5, 1995

[54] ARTIFACT REDUCTION BY Z-DEPENDENT FILTRATION OF THREE-DIMENSIONAL CONE BEAM DATA

[75] Inventor: Hui Hu, Waukesha, Wis.

[73] Assignee: General Electric Company, Milwaukee, Wis.

[21] Appl. No.: 278,368

[22] Filed: Jul. 21, 1994

[51] Int. Cl.⁶ ............................ A61B 6/03; G01N 23/083
[52] U.S. Cl. ................................................. 378/4; 378/901
[58] Field of Search .................. 378/4, 901; 250/363.04

[56] References Cited

U.S. PATENT DOCUMENTS

| | | | |
|---|---|---|---|
| 5,396,528 | 3/1995 | Hu et al. | 378/14 |
| 5,400,255 | 3/1995 | Hu | 364/413.19 |
| 5,400,377 | 3/1995 | Hu et al. | 378/8 |
| 5,416,815 | 5/1995 | Hsieh | 378/4 |

OTHER PUBLICATIONS

*Practical cone-Beam Algorithm*, J. Opt. Soc. Am. A/vol. 1, No. 6/Jun. 1984, pp. 612–619, Feldkamp, et al.

Primary Examiner—David P. Porta
Assistant Examiner—David Vernon Bruce
Attorney, Agent, or Firm—Quarles & Brady

[57] ABSTRACT

A cone beam scanning apparatus reduces image artifacts incident to cone beam geometry by decomposing an acquired image into soft tissue and bone and air images based on the density of the pixels in that image The soft tissue image is filtered to remove image artifacts caused by zones of incomplete frequency space data in the original projection image and is recombined with the bone and air image. The filtering applied is dependent on the location of the reconstructed image along the z-axis.

5 Claims, 4 Drawing Sheets

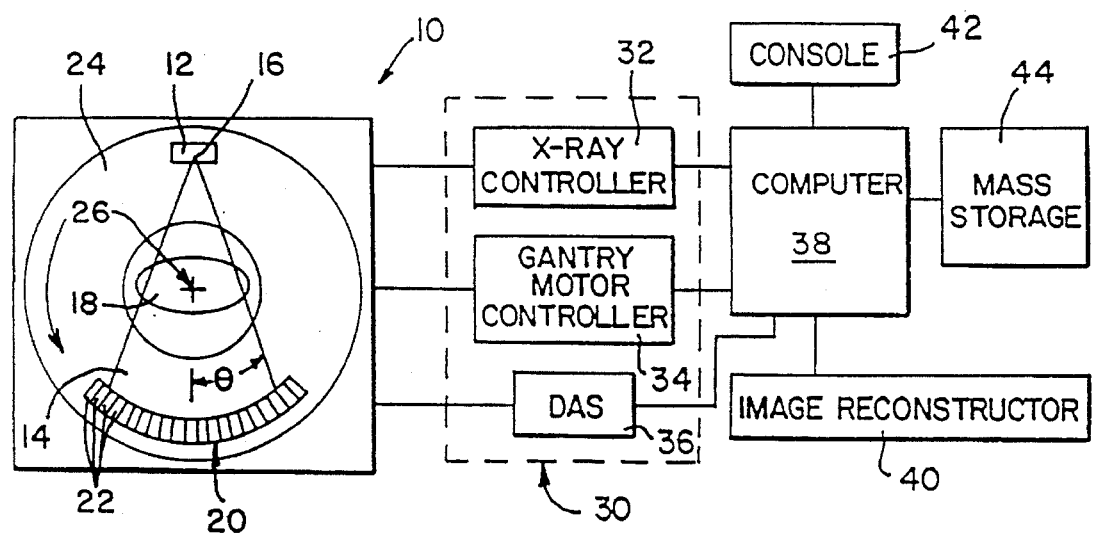
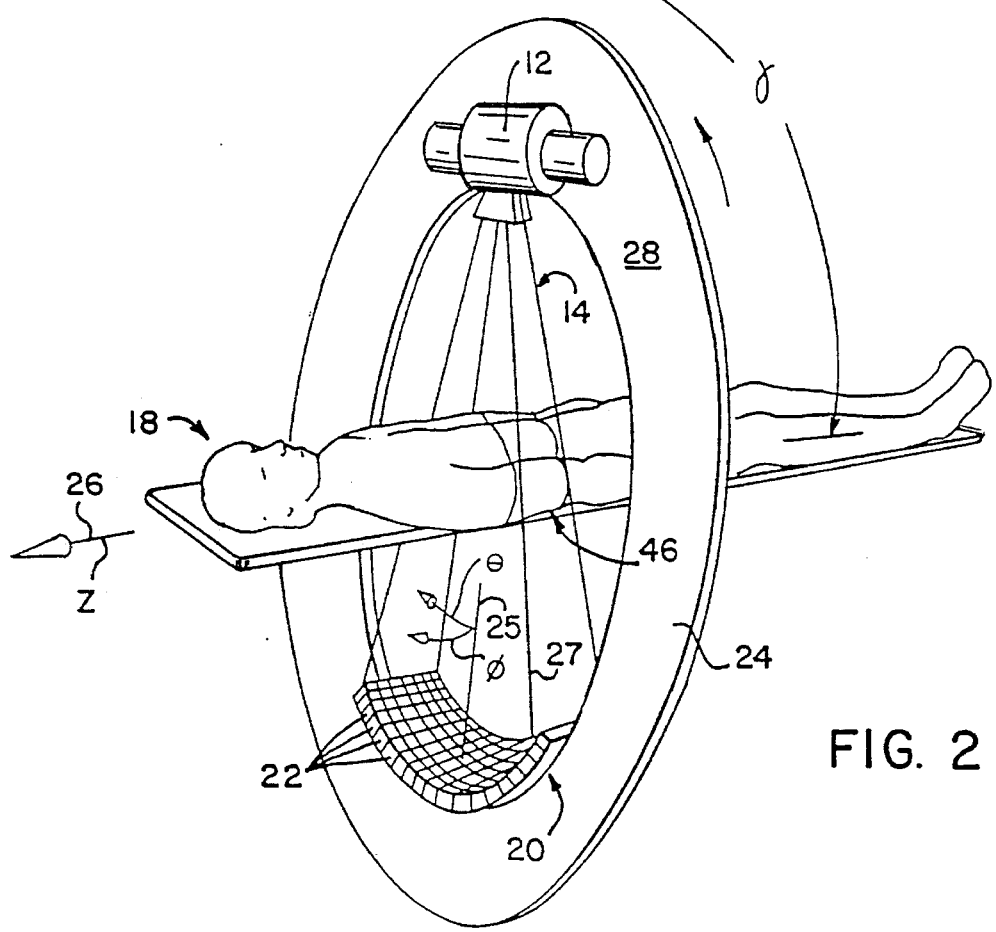

ARTIFACT REDUCTION BY Z-DEPENDENT FILTRATION OF THREE-DIMENSIONAL CONE BEAM DATA

FIELD OF THE INVENTION

This invention relates to computed tomography (CT) and other similar projection imaging systems and specifically to volumetric CT systems in which projections of the imaged object are taken along rays within a gantry plane and rays crossing the gantry plane.

BACKGROUND OF THE INVENTION

In a typical computed tomography system, an x-ray source, mounted to a rotating gantry, is collimated to form a fan beam with a defined fan beam angle. The fan beam is typically oriented to lie within the "gantry plane' normal to the axis of rotation of the gantry, and is transmitted through an imaged object to an x-ray detector array also oriented within the gantry plane. The axis of rotation of the gantry is also referred to as the z-axis.

The detector array is comprised of a line of detector elements, each of which measures the intensity of transmitted radiation along a ray projected from the x-ray source to the particular detector element. The intensity of the transmitted radiation is dependent on the attenuation of the x-ray beam along that ray by the imaged object.

The x-ray source and detector array may be rotated on the gantry within the gantry plane and around a center of rotation so that the "gantry angle" at which the fan beam axis intersects the imaged object may be changed. At each gantry angle, a projection is acquired comprised of the collected intensity signals from each detector element. The gantry is then rotated to a new angle and the process is repeated to collect projection data along a number of gantry angles to form a 2D tomographic projection set. The acquired tomographic projection sets are typically stored in a numerical form for later computer processing to "reconstruct" a slice image according to reconstruction algorithms known in the art.

As the resolving power of computed tomography methods increases, a growing number of slices are required in the z-dimension. One method of decreasing the scanning time needed to collect such multiple slices of data is to acquire projection data for more than one slice during a given gantry rotation. This may be done by using a two-dimensional detector array extending along the z-axis to obtain projection data on either side of the gantry plane, and by changing the collimation of the x-rays from that of a fan beam to a cone beam having rays diverging from a focal spot not only within the gantry plane but to either side of the gantry plane as well. As with fan beam CT, projection data is acquired at a series of gantry angles about the patient to produce a projection data set. In this case, however, it is a 3D projection data set.

A number of techniques are known in the art for reconstructing images from a 3D projection data set produced by a cone beam. One such technique is described in the paper: "Practical cone-beam algorithm" by L. A. Feldkamp, et al. J. Opt. Soc. Am. A/Vol. 1, No. 6, (June 1984) which is hereby incorporated by reference. As described in co-pending U.S. patent application Ser. No. 093,108, now U.S. Pat. No. 5,400, 377, filed on Jul. 16, 1993 and entitled "Artifact Reduction Method For Tomographic Image Reconstruction Using Cross-Plane Rays", artifacts are produced in the reconstructed images due to the incomplete data. A filtering technique is presented in this co-pending patent application which significantly reduces these artifacts, but it has been discovered that the particular filter proposed therein can be significantly improved to further reduce image artifacts.

SUMMARY OF THE INVENTION

The present invention is a method and apparatus for reducing artifacts caused by cone beam reconstruction techniques. The present invention recognizes that a class of such artifacts are caused by missing projection data bounded by conical zones in the frequency space representation of such projection data. Based on prior knowledge about the type of objects to be imaged, images are filtered in the Fourier domain using a filter which changes as a function z axis location of the projection data. Specifically, in the present invention, projection data is acquired in a cone beam scan and reconstructed by cone beam reconstruction techniques to produce a first tomographic image having pixels representing varying densities of the imaged object. This first tomographic image is separated into two images, a mid-range density image having pixels with density values within a predetermined range, and an extreme-range density image having pixels with density values outside of the predetermined range. In the human body, the mid-range image may be soft tissue and the extreme-range image may be bone and air.

The mid-range density image is then filtered to reduce artifacts in the zones of missing frequency space data. It has been discovered that the filter used in this step should be matched to that required at the z location of the projection data being filtered if image artifacts are to be minimized. Accordingly, a set of z-dependent filter kernels are calculated for the CT scanner and used in this step to separately filter each slice of projection data. This filtered mid-range image is then recombined with the extreme-range image to produce a second tomographic image having reduced image artifacts.

In the preferred embodiment the z-dependent filtering of the mid-range image data is accomplished by Fourier transforming the mid-range image data on a slice-by-slice basis and multiplying each slice of transformed image data by a Fourier transformed filter kernel designed for the particular z-axis position of the slice. Each filtered slice is then transformed back to image space and combined with the extreme-range image data as described above. The filter kernel for each slice is produced by measuring the impulse response of the CT scanner at several locations along the z-axis to develop a filter kernel as a function of z location. At each z location of a slice, this filter kernel is Fourier transformed slice-by-slice and stored for use in the image reconstruction filtering process described above.

BRIEF DESCRIPTION OF THE DRAWINGS

FIG. 1 is a simplified schematic representation of a CT system, as may be used with the present invention, including a gantry holding an x-ray source and x-ray detector for obtaining projections of a patient;

FIG. 2 is a simplified perspective view of the gantry of FIG. 1 showing a cone beam of x-rays from the x-rays source and a two-dimensional detector array suitable for three dimensional scanning;

DESCRIPTION OF THE PREFERRED EMBODIMENT

Figure 3:
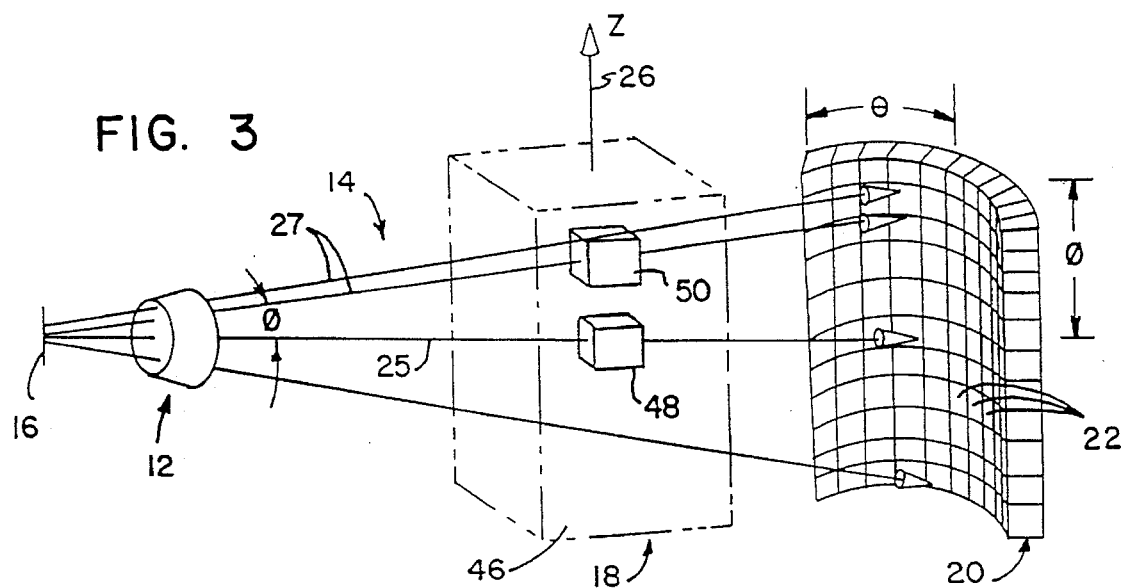
FIG. 3 is a geometric representation of a volume of the patient as illuminated by the cone beam of x-rays showing the parallelism of cross-plane rays for small subvolumes.

Referring to FIGS. 1 and 2, a CT system 10 includes an x-ray source 12 oriented to project a cone beam of x-rays 14 from a focal spot 16 through a patient 18 to be received by a two-dimensional detector array 20. The two-dimensional detector array 20 includes a number of detector elements 22 arranged over the area of the detector array 0 in generally perpendicular columns and rows to detect a projected image of the x-rays 14 passing through the patient 18.

The x-ray source 12 and the two-dimensional detector array 20 are mounted on either side of a gantry 24 so as to rotate about an axis of rotation 26 generally positioned within the patient 18. The axis of rotation 26 forms the z-axis of a Cartesian coordinate system having its origin centered within the cone beam 14. The plane defined by the x and y axes of this coordinate system thus defines a plane of rotation, specifically the gantry plane 28 of the gantry 24.

Rotation of the gantry 24 is measured by angle $\gamma$ from an arbitrary reference position within the gantry plane 28. Angle $\gamma$ varies between 0 and $2\pi$ radians (360°). The x-rays of the cone beam 14 diverge from the gantry plane 28 by angle $\phi$ and diverge along the gantry plane 28 by angle $\theta$. The two-dimensional detector array 20 is arranged as a section of the surface of a sphere or a cylinder having a center at the focal spot 16, and its array of detector elements 22 is arranged to receive and make intensity measurements along the rays of the cone beam 14 throughout the angles of $\phi$ and $\theta$ of the cone beam 14. Rays 25 of the cone beam 14 in the gantry plane 28 (i.e., $\theta=0$) will be termed "in-plane rays". The in-plane rays 25 are those rays used in conventional fan beam CT systems. Those rays 27 lying outside this plane will be termed "cross-plane rays".

Referring to FIG. 1, the control system of the CT scanner 10 has gantry associated control modules 30 which include: x-ray controller 32, which provides power and timing signals to the x-ray source 12, gantry motor controller 34, which controls the rotational speed and position of the gantry 24, and data acquisition system (DAS) 36, which receives projection data from the two-dimensional detector array 20 and converts the data into digital form for later computer processing, while preserving the values of $\phi$, $\theta$ and the gantry angle $\gamma$ at which the data was taken. The x-ray controller 32, the gantry motor controller 34 and the data acquisition system 36 are connected to computer 38.

The computer 38 is a general purpose mini-computer programmed to acquire and manipulate projection data as will be described in detail below. The computer 38 is connected to an image reconstructor 40 which performs high speed image reconstruction according to methods known in the art.

The computer 38 receives commands and scanning parameters via operator console 42 which is generally a CRT display and keyboard that enables an operator to enter parameters for the CT scan and to display the reconstructed image. A mass storage device 44 provides a means for storing operating programs.

Referring to FIG. 3, for a given projection, the cone beam of x-rays 14 strikes a volume 46 of the patient 18. Within that volume 46, a first subvolume 48 receives in-plane rays 25 from the cone beam 14 having a $\phi$ value of zero. These in-plane rays are detected by the detector elements 22 of the two-dimensional detector array 20 within the gantry plane 28 (shown in FIG. 2).

A second subvolume 50, displaced along the z-axis from the first subvolume 48, receives cross-plane rays 27 having $\phi$ values not equal to zero. These cross-plane rays 27 are detected by other rows of detector elements 22 of the two-dimensional detector array 20, such rows not lying within the gantry plane 28. Provided subvolume 50 is small, the cross-plane rays intercepting subvolume 50 are essentially parallel to each other.

Figure 4:
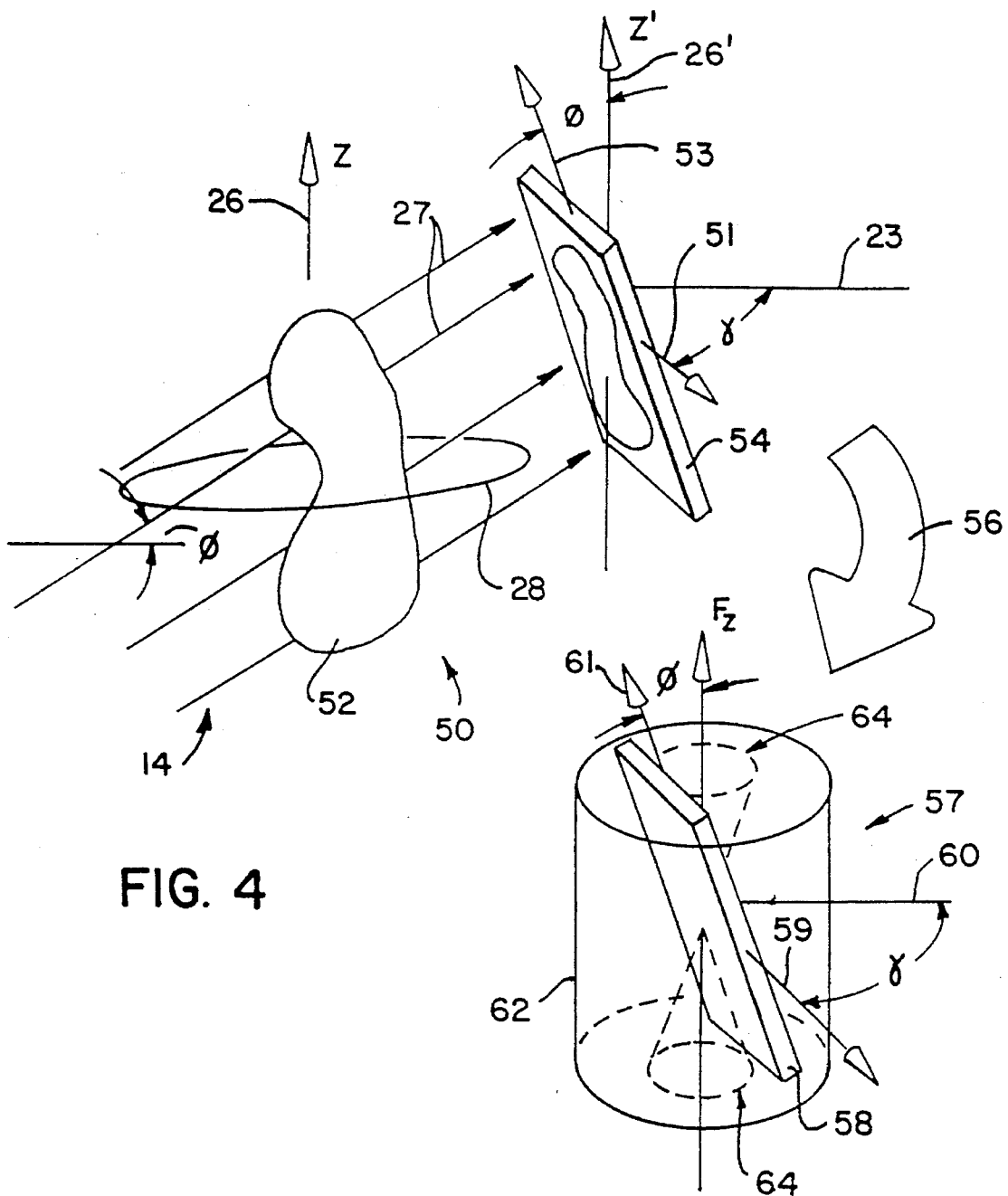
FIG. 4 is a diagrammatic representation of the *Three Dimensional Fourier Slice Theorem* showing the generation of frequency space data from multiple projections of cross-axis rays.

Referring to FIG. 4, during scanning, an object 52 within sub-volume 50 is illuminated by essentially parallel cross-plane rays 27 to create a parallel, two-dimensional projection 54. The plane of projection 54 is perpendicular to the cross-plane rays 27, i.e., the normal to the plane 54 is parallel to rays 27, and is centered on a Z'-axis 26' parallel to Z-axis 26.

Referring still to FIG. 4, the *Three Dimensional Fourier Slice Theorem* states that the two-dimensional Fourier transform of a two-dimensional parallel projection of an object provides a plane of values of three-dimensional Fourier transform of the object, where the normal to the plane of values in frequency space plane is parallel to the direction of the projection. Accordingly, the two-dimensional parallel projection 54, when operated on by a two-dimensional Fourier transform 56 provides a plane 58 of data in frequency space 57.

The two-dimensional projection 54 has a first axis 51 perpendicular to the Z'-axis 26' and a second axis 53 tipped with respect to the Z'-axis 26' by angle $\phi$ so as to receive the cross-plane rays 27 of the cone beam 14 perpendicularly to its surface. The first axis 51 of the two-dimensional projection 54 is rotated around the Z'-axis 26' by an amount $\gamma$ from reference angle 23 determined by the position of the gantry 24, as previously described.

Similarly, by the above theorem, the two-dimensional Fourier transform 56 of the two-dimensional projection 54 yields the values of the three-dimensional Fourier transform of the object 52 in frequency space 57 along a plane 58 having a first axis 59 rotated by angle $\gamma$ around perpendicular frequency space axis $F_z$ with respect to a reference 60, and a second axis 53 rotated by angle $\phi$ with respect to $F_z$. The axis $F_z$ is simply a Cartesian coordinate axis of frequency space 57 defined as corresponding to the Z-axis 26.

For different projections 54 obtained at different angles $\gamma$ by rotation of gantry 24, additional planes 58 of Fourier data will be obtained. Each plane 58 of Fourier data will have the same angle $\phi$ with respect to $F_z$, as fixed by the angle $\phi$ of the cross-plane rays 27, but will be rotated around $F_z$ so as to sweep out a cylinder of data 62 in frequency space 57 excluding two conical areas 64. The excluded conical areas 64 are cones having bases abutting the bases of the cylinder 62 and vertices meeting at the centerpoint of cylinder 62.

The vertex angle of these conical areas 64 is equal to 2φ, and thus the conical areas grow larger as the φ value of the cross-plane rays 27 increases. The cylinder 62 and the cones 64 bound the data obtained in frequency space for projections 54 taken at angles of } ranging over 2π radians during rotation of the gantry 24.

Referring to FIG. 3, in a cone beam, the angle φ of a given volume element 50 will vary as the volume element is displaced along the z-axis. Accordingly the cone of missing data 64 will have a vertex angle that is progressively greater as the volume element 50 moves away from the gantry plane 28. Nevertheless, the missing data 64 of the entire projection set for the volume 46 may be approximated as a single conical area having an apex angle between 0 and twice the maximum value of φ in the cone beam 14.

Referring again to FIG. 4, reconstruction of an image of the object 52 requires taking the inverse Fourier transform of the data of cylinder 62. Generally this inverse Fourier transform is taken along a single plane at a time through cylinder 62 so as to produce a tomographic or slice image. The effect of the missing data of the conical areas 64 on the reconstructed image is to eliminate spatial frequencies that are high in $F_z$ but low in $F_x$ and $F_y$ from the reconstructed image for slices above and below the gantry plane 28. It can be shown that cone beam reconstruction techniques assume that data in the missing data cones 64 are zero.

Figure 5:
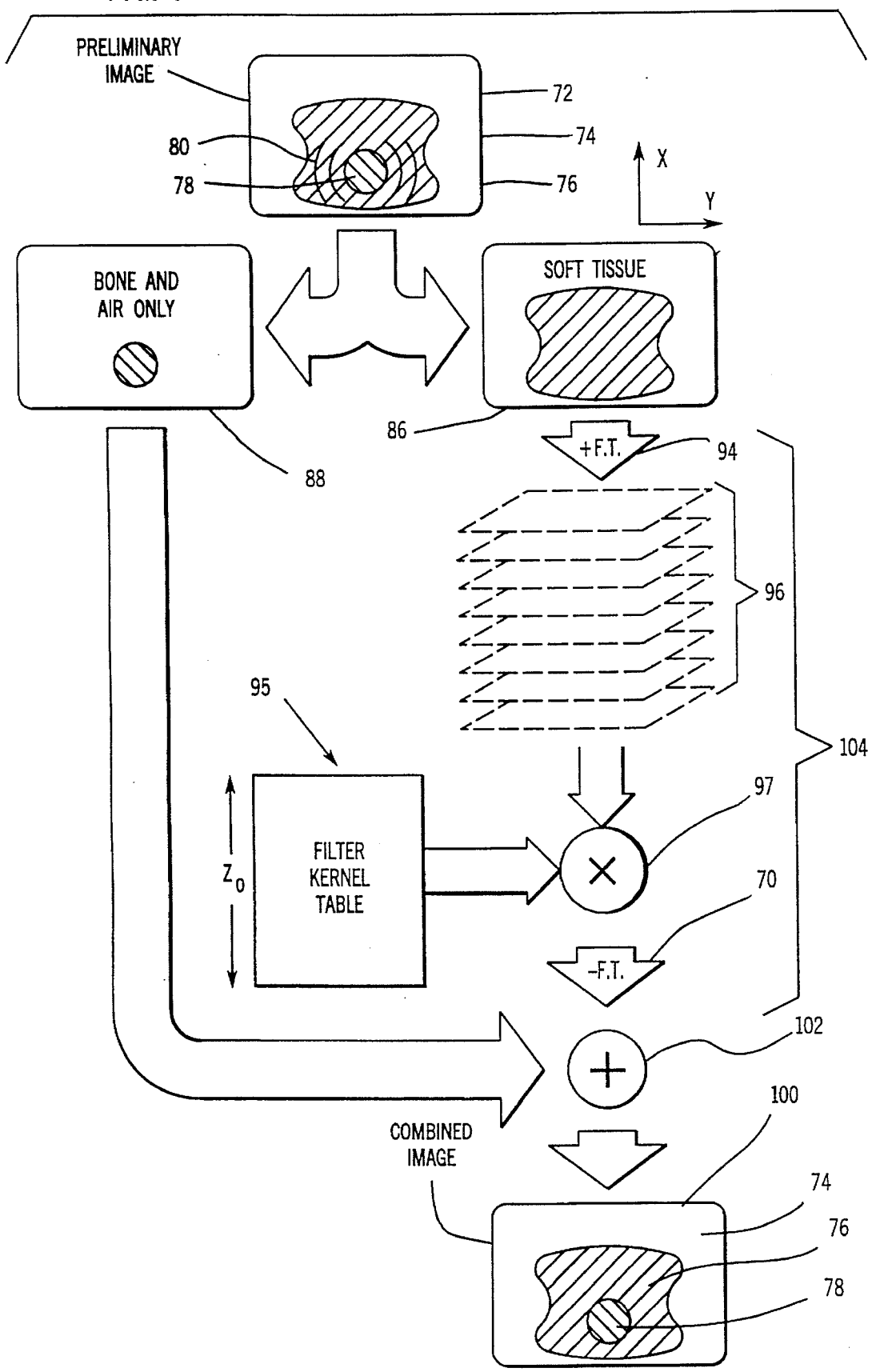
FIG. 5 is a pictorial representation of the artifact attenuation process of the present invention showing first the image decomposed into mid and extreme range images, and next, the mid-range image transformed slice-by-slice into a frequency space representation where they are filtered and then recombined with the extreme-range image.

Referring now to FIG. 5, the acquired conical projection set data provides frequency space data 62 having conical area 64 of missing frequency space data. The Fourier transform 70 of this frequency space data 62 provides a preliminary image 72 having pixels representing air 74, soft tissue 76, bone 78 and image artifacts 80.

Figure 6:
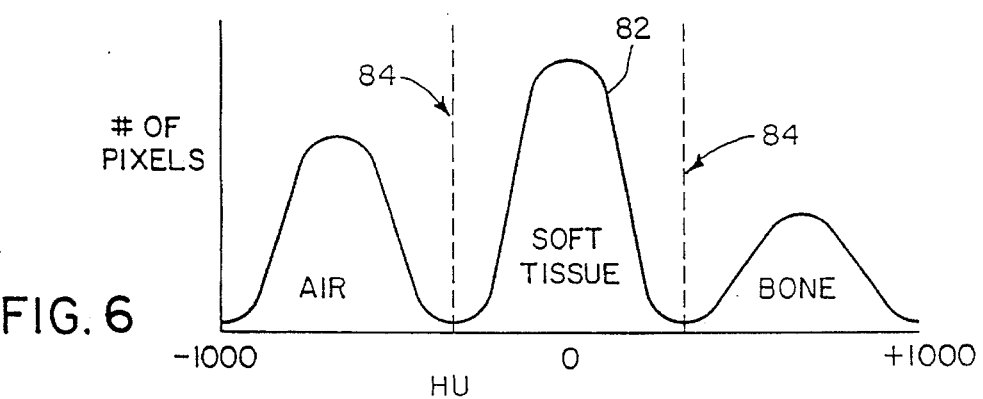
FIG. 6 is a histogram of pixels vs. pixel density for a typical tomographic image of the human body prior to artifact reduction of the present invention showing the groupings of the pixels into distinct ranges of bone, air and soft tissue.

Referring to FIGS. 5 and 6, each pixel of the preliminary image 72 has an associated density value typically represented in the image as a gray level from white to black. The density for CT machines is typically quantified as Houndsfield units (HU) ranging from +1,000 (white) to −1,000 (black). In images of the human body, the pixels will generally cluster into one of three groupings of air, soft tissue and bone having progressively increasing HU, or densities. The divisions between these categories may be readily determined by plotting the density of each pixel of the image against the number of pixels having that value to provide a tri-modal histogram having a central lobe 82 flanked by two minima 84 which define a range of HU corresponding to pixels depicting soft tissue within the body.

Referring still to FIG. 5, by employing the range established by the minima 84, each pixel of the image 72 may be categorized as either soft tissue or non-soft tissue (bone and air). The air of concern is typically that entrained within the lungs or stomach cavity but may also be the air generally surrounding imaged objects. After categorizing each pixel of the preliminary image 72, two images 86 and 88 are produced. The first image is an image 86 of soft tissue only and the second image is an image 88 of bone and air. The "spaces" in the soft tissue image 86 formerly occupied by bone and air are "padded" with an average value pixel and the bone and air image 88 is the difference between midrange image 86 and the original image 72.

As disclosed in the above-cited co-pending U.S. patent application Ser. No. 093,108, the soft tissue image 86 may be operated on by a 3-D Fourier transform to provide frequency space data for the soft tissue image 86. The resulting data within the cone 64 for this soft tissue image 86 will include data that contributes to the image artifacts 80. This data was removed using a filter which is applied to each element of the 3D frequency space data set. It is the primary teaching of the present invention that this filtering step can be substantially improved by applying a filter which changes as a function of slice position along the Z-axis.

It can be demonstrated that the conical regions 64 are not constant, but instead, are different at each slice location $(z_o)$ along the Z-axis. In other words, the preliminary image reconstruction method modulates the true image differently for different Z locations of the slice being reconstructed. However, it can also be shown that the filter may be fixed for any particular slice location. Accordingly, a set of filters are derived as will now be described, and these are applied to the corresponding image slices.

The z-dependent filter can be written to the first order approximation as $h(\vec{\rho} - \vec{\rho}_0, z, z_0)$. Then the general D convolution relation which applies this filter to the tissue image $f_t(\vec{\rho}_0, z_0)$ can be written as:

$$f_t'(\vec{\rho},z) = \int f_t(\vec{\rho}_0,z_0) h(\vec{\rho}-\vec{\rho}_0,z,z_0) d\vec{\rho}_0 dz_0 \qquad (1)$$

where:
$\vec{\rho}_0$ = location within a slice
$z$ = is the location along the z axis of the reconstructed slice
$\vec{\rho}$ = location in the slice being reconstructed
$z_0$ = location along the slice direction.

Because of the z-dependent nature of the filter, the above 3D convolution integral cannot be reduced to a simple form. However, since the stationary property still holds in the x and y dimensions, reductions in complexity can still be carried out in these two dimensions. As a result, the 3D convolution integral of equation (1) can be reduced to the following 1D convolution integral:

$$\sim F_t'(\omega_p, z) = \int \sim F_t(\omega_p,z_0) \sim H(\omega_p,z,z_0) dz_0 \text{ for each } \omega_p \qquad (2)$$

where $\omega_p$ is a point in a special frequency space derived by slice-by-slice 2D Fourier transformations along x and y of the 3D data set, and $\sim F_t'(\omega_p,z)$, $\sim F_t(\omega_p,z_0)$ and $\sim H(\omega_p,z,z_0)$ are the slice-by-slice 2D Fourier transforms (x and y dimensions) of $f_t'$, $f_t$ and $h$ in Equation (1).

As $z_0$ becomes smaller or $\omega_p$ becomes larger, the filter kernel $\sim H(\omega_p,z,z_0)$ is more like the ideal impulse. Especially at the center plane $(z_0=0)$, no low-pass filtration is carried out. However, the kernel $\sim H(\omega_p,z,z_0)$ becomes broader (or, narrower in bandwidth in its Fourier domain) as $z_0$ becomes larger or $\omega_p$ becomes smaller. This z-dependent low-pass filter correctly reflects the z dependence of the artifacts.

The filter kernels $\sim H(\omega_p,z,z_0)$ for each slice location are determined by the particular parameters of each CT system. These are determined by a series of measurements in which a small dense ball is imaged at each slice location $z_0$. The ball is placed near the central axis 26 and it is scanned to produce a 3D image which represents the impulse response of the CT system $h(\vec{\rho}-\vec{\rho}_0,z,z_0)$ at that slice location $z_0$. The filter kernel $\sim H(\omega_p,z,z_0)$ for that slice $(z_0)$ is then calculated by performing a 2D Fourier transformation (x and y dimensions) for each z in the 3D image. This filter kernel is stored in a table 95 (FIG. 5) and the process is then repeated after moving the dense ball to the next $z_0$ slice position. The filter kernels are preferably measured at every slice locations $z_0$, although it can be appreciated by those skilled in the art that fewer measurements can be made and interpolation used to fill in the complete set of filter kernels stored in the table 95.

Referring again to FIG. 5, the invention is implemented by first Fourier transforming each slice $(z_0)$ of the 3D soft tissue image 86. As indicated at 94, this is a 2D Fourier transformation along the x and y dimensions, and the result is a set of 2D slices 96 in frequency space. The set of 2D slices 96 is then filtered using the corresponding filter kernel stored in the table 95. This is a matrix multiplication as indicated at 97, and resulting filtered 2D slices are then transformed back to object space by a 2D inverse Fourier transformation 70.

The inverse Fourier transform 70 produces a revised soft tissue image slice (not shown) which is added to the corresponding slice in the bone and air image 88 to produce a new image 100 having reduced image artifacts. This combination is a simple pixel by pixel addition of the bone and air image slices 88 and the soft tissue image slices 86 as modified by the filtering process 104 comprising the slice-by-slice Fourier transform 94, the filtering process 97 and the slice-by-slice inverse Fourier transform 70. The summation is accomplished by adder 102.

It will be recognized that the filtering of the images does not necessarily require an actual conversion of the images into frequency space and operation on the frequency space data as described above, but that other mathematical techniques such as convolution may be employed to perform the same function in object space. Also, the filtering of the image may only need to be carried out for those points with large z and small $\omega_p$.

Other modifications of the preferred embodiment which will be within the spirit and scope of the invention will be apparent to those with ordinary skill in the art. For example, the techniques described herein may be applied to other imaging modalities such as SPECT and positron emission tomography where the source of cross-plane and in-plane rays is a decaying isotope within the body or "fourth generation" CT scanning where a stationary detector array receives radiation from an orbiting radiation source.

We claim:

1. A method of reducing image artifacts in a tomographic image of an imaged object, such artifacts resulting from simultaneous multiple slice acquisitions of projection data, comprising the steps of:

(a) acquiring a set of projection data at a plurality of angles about an axis through the image object, the projection data measuring attenuation along first rays passing through the imaged object perpendicular to the axis, and second rays passing through the imaged object but not perpendicular to the axis, wherein the set of projection data transformed into frequency space has zones of missing frequency space data as a result of the non-perpendicular angle of the second rays;

(b) reconstructing the projection data to produce a three-dimensional tomographic image data set having pixels of varying density;

(c) separating the three-dimensional tomographic image data set into a mid-range density image data set including pixels having density values within a predetermined range, and an extreme-range density image data set including pixels having density values outside of the predetermined range;

(d) spatially filtering the mid-range density image data set to reduce the value of its spatial frequency in frequency zones corresponding to the zones of missing frequency space data of the projection set with a filter that changes as a function of the location of the pixel value along said axis; and (e) combining the filtered mid-range density image data set and the extreme-range density image data set to create a tomographic image.

2. A method of claim 1 wherein step (d) of filtering the mid-range density image includes the steps of:

(i) performing a two-dimensional Fourier transformation on mid-range image data at a selected slice location along said axis;

(ii) filtering the slice of transformed mid-range image data with a filter kernel whose value depends on the location of said slice along said axis; and (iii) inverse Fourier transforming the filtered slice of mid-range image data.

3. The method as recited in claim 2 in which the filtering is performed on mid-range image data at a plurality of selected slice locations along said axis and the filtered slices of mid-range image data is combined with the extreme-range density image data located at corresponding slice locations along said axis to produce a corresponding plurality of tomographic images.

4. An apparatus for producing tomographic images of an imaged object from simultaneous multiple slice acquisitions of projection data, the tomographic images having reduced image artifacts the apparatus comprising;

(a) a two dimensional detector array for rotating about an axis and the imaged object for acquiring projection data measuring attenuation by the imaged object along first rays passing through the imaged object perpendicular to the axis, and second rays passing through the imaged object but not perpendicular to the axis, wherein the set of projection data transformed into frequency space has zones of missing frequency space data as a result of the non-perpendicular angle of the second rays;

(b) a reconstruction means for reconstructing the projection data to produce a three-dimensional tomographic image having pixels of varying density;

(c) a selection means receiving the three-dimensional tomographic image for dividing the three-dimensional tomographic image into a mid-range density image including pixels having density values within a predetermined range and an extreme-range density image including pixels having density values outside of the predetermined range;

(d) a filter receiving a slice of the mid-range density image for reducing the value of its spatial frequency in frequency zones corresponding to the zones of missing frequency space data of the projection set to create a slice of filtered mid-range density image; and (e) a combining means for combining the slice of filtered mid-range density image with a corresponding slice of the extreme-range density image to create a tomographic image;

wherein the amount of filtering applied in step (d) is dependent on the location of said slice along said axis.

5. The apparatus as recited in claim 4 in which the filter includes:

(i) means for Fourier transforming the slice of mid-range density image along two dimensions;

(ii) a filter kernel table for storing a plurality of filter kernels corresponding to slice locations along said axis;

(iii) a multiplier for applying one of the stored filter kernels to the transformed slice of mid-range density image; and (iv) means for performing an inverse Fourier transform on the filtered slice of mid-range density image.

* * * * *